United States Patent
Desmots et al.

(10) Patent No.: US 6,306,380 B1
(45) Date of Patent: Oct. 23, 2001

(54) COSMETIC DEPILATORY COMPOSITIONS COMPRISING A CONTINUOUS AQUEOUS PHASE AND AN OIL PHASE

(75) Inventors: Sarah Desmots, Dreux; Bruno Guillaume, Prunayen Yvelines; Philippe Ledon, Saint Prest; Veronique Pires, Mainvilliers, all of (FR)

(73) Assignee: Reckitt & Colman France, Massey Cedex (FR)

( * ) Notice: Subject to any disclaimer, the term of this patent is extended or adjusted under 35 U.S.C. 154(b) by 0 days.

(21) Appl. No.: 09/462,331

(22) PCT Filed: Jun. 26, 1998

(86) PCT No.: PCT/GB98/01878

§ 371 Date: Apr. 7, 2000

§ 102(e) Date: Apr. 7, 2000

(87) PCT Pub. No.: WO99/02125

PCT Pub. Date: Jan. 21, 1999

(30) Foreign Application Priority Data

Jul. 9, 1997 (EP) .................................................. 97401638
Sep. 26, 1997 (GB) .................................................. 9720372

(51) Int. Cl.$^7$ ........................... A61K 7/155; A61K 9/107
(52) U.S. Cl. ........................... 424/73; 424/70.1; 514/770; 514/783; 514/938
(58) Field of Search ........................... 424/73, 70.1, 401, 424/70.4, 70.5, 70.51, 70.22, 70.27, 70.31

(56) References Cited

U.S. PATENT DOCUMENTS

| 4,121,904 | 10/1978 | Schamper ................................. 8/161 |
| 4,177,260 | 12/1979 | Warjaroff ............................... 424/71 |
| 5,645,825 | 7/1997 | Hillebrand et al. .................... 424/73 |

FOREIGN PATENT DOCUMENTS

| 0 085 894 A2 | 8/1983 | (EP) . |
| 0 095 916 A2 | 12/1983 | (EP) . |
| 1 513 659 | 6/1978 | (GB) . |
| 2 306 323 A | 5/1997 | (GB) . |
| WO91/10421 | 7/1991 | (WO) . |
| WO93/08791 | 5/1993 | (WO) . |
| WO94/21216 | 9/1994 | (WO) . |

OTHER PUBLICATIONS

Copy of PCT International Search Report for PCT/GB98/01878 dated Oct. 29, 1998.

Primary Examiner—James M. Spear
(74) Attorney, Agent, or Firm—Fish & Richardson P.C.

(57) ABSTRACT

The invention provides depilatory compositions comprising: (a) a continuous aqueous phase; (b) a depilatory agent; and (c) at phase comprising (i) a non-polar coil separated from the continuous aqueous phase by a bilayer phase comprising (ii) a surfactant; (iii) a polar substance; wherein the composition is substantially free from tertiary amines; processes for their preparation; and their use degrading hair keratin.

17 Claims, No Drawings

COSMETIC DEPILATORY COMPOSITIONS COMPRISING A CONTINUOUS AQUEOUS PHASE AND AN OIL PHASE

This application is a 371 of PCT/GB98/01878 file Jun. 26, 1998.

The present invention relates to depilatory compositions in the form of an improved oil-in-water emulsion; their preparation; and their use in degrading hair keratin.

BACKGROUND OF THE INVENTION

Compositions for removing superfluous body hair are well known and are of various types. One type of composition requires initial heating before being applied to the skin in a generally molten state. It is then allowed to solidify before being removed from the skin together with unwanted hair.

Another type of depilatory composition is in the form of a cream, which can be applied to the skin at room temperature. The cream includes a substance that degrades hair keratin. Such substances tend to irritate the skin which is a problem for users with sensitive skin. Compositions with reduced irritancy have been sought.

SUMMARY OF THE INVENTION

The present invention therefore provides a depilatory composition comprising:
(a) a continuous aqueous phase;
(b) a depilatory agent; and
(c) an oil phase comprising
 (i) a non-polar oil separated from the continuous aqueous phase by a bilayer phase comprising
 (ii) a surfactant; and
 (iii) a polar substance;
wherein the composition is substantially free from tertiary amines.

However, the present inventors do not wish to be bound by the definition of the particular structure of the composition that they believe to be formed. According to the present invention, there is further provided a depilatory composition comprising from 2% to 6% w/w of depilatory agent, from 0.2% to 20% w/w of non-polar oil, from 2% to 20% w/w of surfactant, from 0.5% to 20% w/w of polar substance and from 95.3% to 34% w/w of aqueous phase; wherein the composition is substantially free from tertiary amines.

DETAILED DISCLOSURE

The depilatory agent is a substance capable of degrading keratin and may be, for example, a sulphur compound such as potassium thioglycolate, dithioerythritol, thioglycerol, thioglycol, thioxanthine, thiosalicylcic acid, N-acetyl-L-cysteine, lipoic acid, $NaHSO_3$, $Li_2S$, $Na_2S$, $K_2S$, $MgS$, $CaS$, $SrS$, $BaS$, $(NH_4)_2S$, sodium dihydrolipoate 6,8-dithiooctanoate, sodium 6,8-dithiooctanoate, salts of hydrogen sulphide for example NaSH or KSH, thioglycolic acid, thioglycerol, 2-mercaptopropionic acid, 3-mercaptopropionic acid, thiomailic acid, ammonium thioglycolate, glyceryl monothioglycolate, monoethanolamine thioglycolate, monoethanolamine thioglycolic acid, diammonium dithiodiglycolate, ammonium thiolactate, monoethanolamine thiolactate, thioglycolamide, homocysteine, cysteine, glutathione, dithiothreitol, dihydrolipoic acid, 1,3-dithiopropanol, thioglycolamide, glycerylmonothioglycolate, thioglycolhydrazide, keratinase, hydrazine sulphate, hydrazine disulphate, triisocyanate, guanidine thioglycolate, hair reducing pack, calcium thioglycolate and/or cysteamine. However, the composition is preferably substantially or, more preferably, completely free from depilatory agents that destroy the thermodynamic equilibrium or the surface tension of the composition; examples of such agents include alkali metal sulphides. Preferably, the composition comprises from 2.0% to 6.0% w/w of the keratin-degrading substance in order to obtain a satisfactory depilation time of about 5 minutes.

It is preferred that the non-polar oil is in the form of droplets, although it may also be in the form of sheets. When in the form of droplets, each droplet of the non-polar oil is preferably individually surrounded by one or more than one bilayer. When in the form of sheets, each sheet of the non-polar oil is preferably separated from the adjacent sheet by one or more than one bilayer. More preferably, each bilayer, in the case where more than one is present, is itself separated by a bilayer aqueous phase comprising at least water and depilatory agent.

The non-polar oil preferably has a polarity index of from 20 to 46 mN/m, more preferably from 30 to 46 mN/m. The polarity index is a measure of the interfacial surface tension between oil and water. This term is defined and explained in Principles of Colloid and Surface Chemistry, Paul C Hiemenz (2nd edition, Marcel Dekker 1986) incorporated herein in its entirety.

Suitable non-polar oils include thick mineral oils e.g. paraffin oil, sweet almond oil, isohexane, sunflower seed oil, apricot kernel oil, and/or shea butter. The non-polar oil and the polar substance are preferably miscible i.e. a mixture containing 50% of each should exhibit no phase separation. When the non-polar oil is in the form of droplets, these preferably have a diameter of from $0.01\mu$, preferably from $0.1\ \mu m$, to, preferably $10\ \mu m$, more preferably $1\ \mu m$, most preferably $0.5\ \mu m$. Preferably, the composition comprises from 0.2% to 20% w/w, more preferably from 0.2% to 4%, most preferably from 0.5% to 2% w/w of the non-polar oil.

The surfactant and oils in the oil phase are preferably chosen so that the Required Hydrophilic-Lipophilic Balance (RHLB) value of the total oil phase is of the order of the Hydrophilic-Lipophilic Balance (HLB) value of the surfactant. Preferred compositions of this invention are wherein the RHLB value of the total oil phase and the HLB value of the surfactant are substantially equal. THE HLB value is a measure of the hydrophile-lipophile balance as discussed in Encyclopedia of Emulsion Technology, edited by Paul Becher (pages 217–220, volume 1 (1983), Marcel Dekker) incorporated herein by reference in its entirety. The RHLB is explained in Encyclopedia of Emulsion Technology, edited by Paul Becher (pages 353–366, volume 1 (1983), Marcel Dekker) incorporated herein by reference in its entirety.

Preferably, the RHLB value of the total oil phase and the HLB value of the surfactant are each independently from 9 to 12, more preferably from 10 to 11, especially about 10. The polar substance preferably has an RHLB value of from 7 to 16.

In general the surfactant is anionic, cationic or non-ionic. It is preferably non-ionic. Examples of suitable surfactants include ceterayl phosphate, cetearyl alcohol, cetearyl glucoside, cetostearyl alcohol and/or ceteareth 20. It is preferably present in an amount of from 2.0% to 20% w/w, more preferably from 2.0% to 10% w/w, most preferably from 3% to 8% w/w.

The polar substance preferably has a polarity index of from 2 to 15 mN/m, more preferably from 2 to 8 mN/m. The polar substance preferably is a polypropylene oxide-15 sterayl ether, such as that known under the trade designation Arlamol E of ICI Ltd., having a polarity index of about 5.2 mN/m. More preferably the polar substance is a polar oil. Other suitable polar substances are olive oil, macadamia nut oil, avocado oil, calendula oil, wheat germ oil, and/or cyclomethicone optionally admixed with polypropylene oxide-15 stearyl ether.

Preferably, the composition comprises from 0.5 to 20.0% w/w, more preferably from 0.5 to 2%, most preferably from 0.4 to 1% w/w of the polar substance.

Optionally, the composition includes an accelerator that will accelerate the keratin degradation reaction such as urea, thiourea, dimethyl isosorbide (DMI), ethoxydiglycol (Transcutol) or methyl propyl diol (MP diol). Preferably the accelerator is urea or methyl propyl diol. The composition according to the invention preferably comprises from 5% to 15% w/w, more preferably about 8% w/w of an accelerator.

It is particularly preferred for the composition further to comprise an pH regulator to assist in activating the depilatory agent. Preferably the quantity and type of pH regulator is chosen to maintain the pH of the composition at a value greater than 5, preferably greater than 7, more preferably in the range of from 8 to 13, most preferably in the range of from 12 to 12.5, especially about 12. For example, by ensuring that the pH is about 12.1 to 12.5, depilation can occur within about 5 minutes, as desired by the user, without causing undue irritation.

The pH regulator preferably is in the aqueous phase (between the oil droplets) when present. Examples of the pH regulator include arginine (especially L-arginine), silicates (e.g. sodium or potassium silicate), lime and/or polyethyleneimine. It is particularly preferred for the pH regulator also to include lime in an amount of, for example, up to 3% w/w. It is preferred, in order to minimise irritation, for the total content of the pH regulator to be present as less than 3% w/w, more preferably 0.5 to 3% w/w.

In a particularly preferred embodiment of this invention, the depilatory composition includes, in combination, L-arginine, lime, urea, potassium and/or dipotassium thioglycolate, the polar substance and the non-polar oil and aqueous phases.

The compositions of the invention may be formulated into a cream by admixture with a conventional cream base, such as a mixture of polypropylene glycol ester and cetostearyl alcohol. The formulation may also include other ingredients that are conventionally present in depilatory formulations, such as perfumes, oils, and pigments and fillers such as a clay, for example, sodium magnesium silicate, magnesium trisilicate and titanium dioxide. The inclusion of a clay, preferably sodium magnesium silicate, more preferably in an amount of from 0.1 to 10% w/w, most preferably from 0.1 to 1% w/w is particularly advantageous, since this provides sodium and magnesium ions for the buffer system and improves the efficiency of depilation.

The depilatory compositions of the present invention may be prepared by any phase inversion temperature method known in the art for the preparation of oil-in-water emulsions.

Preferably the process for preparing the composition according to the invention comprises mixing the oil phase ingredients together at an elevated temperature of from 50° to 80° C., preferably from 60° C. to 70° C.; adding the aqueous phase ingredients at a temperature of from 70° to 80° C., preferably at about 75° C.; and thereafter adding the depilatory agent at a temperature of from 30° to 40° C., preferably at about 35° C.

An alternative process for preparing a composition according to the invention comprises mixing the non-polar oil and the surfactant together at an elevated temperature of from 50° to 80° C., preferably from 60° C. to 70° C.; adding the aqueous phase at a temperature of from 70° to 80° C., preferably at about 75° C.; and thereafter adding the depilatory agent and polar substance at a temperature of from 30° to 40° C., preferably at about 35° C.

The admixture is preferably effected under conditions of agitation sufficient to aid mixing but insufficient to cause turbulence, more preferably by mechanical means such as stirring. Most preferably the admixture is carried out under conditions having a Reynold value of from 0 to 2000 when the reaction is carried out in a pipe and of from 0 to 10 when the reaction is carried out in a reactor vessel. Preferably the Reynold value is as low as possible. The Reynold value is explained in Althaus, Jakubith Chemistry and Chemical Engineering, memofix 1993 by VCH verlagsgesellschaft.

The depilatory agent is preferably not added until after the oil and aqueous phases have been mixed and gently cooled, for example, to about 30° to 40° C., preferably about 35° C., to prevent degradation of the depilatory agent (which occurs at substantially elevated temperatures). Any optional ingredients may be added thereafter; however it is preferred for the clay to be added when the mixing is carried out at an elevated temperature.

Without wishing to be bound by any particular theory as to the manner in which the preferred depilatory compositions function, it is believed that the oil phase is in the form of discrete droplets enveloped in a bilayer structure comprising molecules of the polar substance sandwiched between molecules of the surfactant. Such bilayer structures are then separated from each other by the continuous aqueous phase (i.e. bilayer aqueous phase) to form a multi-bilayer structure. About 30 to 50% w/w of the keratin-degrading substance tends to be embedded in the surface of this multi-bilayer structure, with the remainder being in the aqueous phase. The embedded keratin-degrading substance is released from the multi-bilayer structure only as it is needed for depilation. Thus, when the keratin-degrading substance in the continuous aqueous phase has been used up in the depilation process, the keratin-degrading substance embedded in the multi-bilayer structure is thermodynamically driven out by entropy and can then diffuse into the hair shaft to effect depilation. In this way, the depilatory composition acts as a reservoir of keratin-degrading substance whose release is regulated during use. Thus the composition according to the invention has the advantage of a lower irritancy. This reduced irritancy is further improved by the absence of tertiary amines from the composition.

According to the invention there is further provided the use of a composition according to the invention to degrade hair keratin.

Throughout this specification, "w/w" refers to the weight of the total composition, unless otherwise specified.

The following Examples illustrate the invention.

EXAMPLE 1

A depilatory composition was prepared from the following ingredients:

| Ingredient | w/w total composition |
| --- | --- |
| Cetostearyl alcohol (2) | 8.0% |
| Sodium magnesium silicate | 1% |
| Ca (OH)$_2$ (3) | 0.5% |
| Urea (3) | 8.0% |
| L-arginine (3) | 2.0% |
| Polyethylenimine (3) | 1.0% |
| Magnesium trisilicate | 0.5% |
| Titanium dioxide (3) | 0.33% |
| Potassium thioglycolate (30%) | 10.0% |
| Shea Butter (1) | 0.5% |
| Perfume | 0.5% |
| Paraffin oil (1) | 3.5% |
| Propylene glycol (3) | 0.26% |
| Acrysol 33 | 0.01% |
| Arlamol E (4) | 1.0% |
| Ceteareth 20 (2) | 3.0% |
| Deionised water | to 100% |

*Acrysol 33 is an acrylic copolymer available from Rohm & Haas.

The method is as follows: the non-polar oils (I) were heated to 60° C., the surfactants (2) added and the mixture stirred in a reactor vessel having a Reynold value of less than 10. Whilst continuing to stir, the temperature was raised to about 75° C. In the meantime, the aqueous phase ingredients (3) were added with about 50% of the water. The aqueous phase as then added, at 75° C., to the oil phase with gentle stirring, and the mixture allowed to cool slowly to 35° C. At this temperature, the active ingredient (4) was added with gentle stirring and then the remaining ingredients.

The resultant cream had a pH of 12.3 and was in the form of discrete droplets formed of the shea butter, at least some of the perfume oil and the paraffin oil, separated by a bilayer structure formed of the cetostearyl alcohol, Ceteareth 20, potassium thioglycolate, some of the propylene glycol and the Arlamol E from a continuous aqueous phase containing the remainder of the ingredients. It satisfactorily removed unwanted hair within about 5 minutes, without causing undue irritation to the skin.

EXAMPLE 2

A depilatory composition was prepared according to the method used in Example 1 from the following ingredients:

| Ingredient | w/w total composition |
| --- | --- |
| Cetostearyl alcohol (2) | 8.0% |
| Sodium magnesium silicate (3) | 1% |
| Ca (OH)$_2$ (3) | 0.5% |
| Urea (3) | 8.0% |
| L-arginine (3) | 2.0% |
| Polyethylenimine (3) | 1.0% |
| Magnesium trisilicate (3) | 0.5% |
| Titanium dioxide (3) | 0.33% |
| Potassium thioglycolate (30%) | 10.0% |
| Shea Butter (1) | 0.5% |
| Perfume (4) | 0.5% |
| Paraffin oil (1) | 3.5% |
| Propylene glycol (3) | 0.26% |
| Acrysol 33 | 0.01% |
| Arlamol E (4) | 1.0% |
| Ceteareth 20 (2) | 3.0% |
| Deionised water | to 100% |

*Acrysol 33 is an acrylic copolymer available from Rohm & Haas.

The composition satisfactorily removed unwanted hair within about 5 minutes, without causing undue irritation to the skin.

EXAMPLE 3

A depilatory composition was prepared according to the method used in Example 1 from the following ingredients:

| Ingredient | w/w total composition |
| --- | --- |
| Cetostearyl alcohol (2) | 8.0% |
| Sodium magnesium silicate (3) | 1% |
| Ca (OH)$_2$ (3) | 0.5% |
| Urea (3) | 8.0% |
| L-arginine (3) | 2.0% |
| Polyethylenimine (3) | 1.0% |
| Magnesium trisilicate (3) | 0.5% |
| Titanium dioxide (3) | 0.33% |
| Potassium thioglycolate (30%) | 10.0% |
| Shea Butter (1) | 0.5% |
| Perfume (4) | 0.5% |
| Paraffin oil (1) | 3.5% |
| Propylene glycol (3) | 0.26% |
| Acrysol 33 | 0.01% |
| Arlamol E (4) | 1.0% |
| Ceteareth 20 (2) | 3.0% |
| Deionised water | to 100% |

*Acrysol 33 is an acrylic copolymer available from Rohm & Haas.

The composition satisfactorily removed unwanted hair within about 5 minutes, without causing undue irritation to the skin.

EXAMPLE 4

A depilatory composition was prepared according to the method used in Example 1 from the following ingredients:

| Ingredient | w/w total composition |
| --- | --- |
| Cetostearyl alcohol (2) | 8.0% |
| Sodium magnesium silicate (3) | 1% |
| Ca (OH)$_2$ (3) | 0.5% |
| Urea (3) | 8.0% |
| L-arginine (3) | 2.0% |
| Polyethylenimine (3) | 1.0% |
| Magnesium trisilicate (3) | 0.5% |
| Titanium dioxide (3) | 0.33% |
| Potassium thioglycolate (30%) | 10.0% |
| Shea Butter (1) | 0.5% |
| Perfume (4) | 0.5% |
| Paraffin oil (1) | 3.5% |
| Propylene glycol (3) | 0.26% |
| Acrysol 33 | 0.01% |
| Arlamol E (4) | 1.0% |
| Montanov 68** (2) | 5.0% |
| Deionised water | to 100% |

*Acrysol 33 is an acrylic copolymer available from Rohm & Haas.
**Montanov 68 is a mixture of cetearyl alcohol and cetearyl glucoside available from Seppic.

The composition satisfactorily removed unwanted hair within about 5 minutes, without causing undue irritation to the skin.

What is claimed is:

1. A depilatory composition in the form of an oil-in-water emulsion which comprises:

from 2% to 6% w/w of a depilatory agent;

from 4.7% to 66% w/w of an oil phase comprising, as a percentage of the depilatory composition, from 0.2% to 20% w/w of a non-polar oil in the form of droplets having a diameter of from 0.01 to 10 $\mu$m and a polarity index of from 20 to 40 mN/m, from 2% to 20% w/w of a surfactant having a HLB value of from 9 to 12, and from 0.5% to 20% of a polar substance having a polarity index of from 2 to 15 mN/m, the oil phase having a RHLB value of from 9 to 12; and from 5.3% to 34% of an aqueous phase comprising L-arginine and lime as pH regulators, wherein the depilatory agent is present in both the oil phase and the aqueous phase and the depilatory composition is substantially free from tertiary amines.

2. A composition according to claim 1 wherein the depilatory agent is selected from the group consisting of potassium thioglycoate, dithioerythritol, thioglycerol, thioglycol, thioxanthine, thiosalicyclic acid, N-acetyl-L-cysteine, lipoic acid, $NaHSO_3$, $Li_2S$, $Na_2S$, $K_2S$, MgS, CaS, SrS, BaS, $(NH_4)_2S$, sodium dihydrolipoate, sodium 6,8-dithiooctanoate, NaSH, KSH, thioglycolic acid, thioglycerol, 2-mercaptopropionic acid, 3-mercaptopropionic acid, thiomalic acid, ammonium thioglycolate, glyceryl monothioglycolate, monoethanolamine thioglycolate, monoethanolamine thioglycolic acid, diammonium dithiodiglycolate, ammonium thiolactate, monoethanolamine thiolactate, thioglycolamide, homocysteine, cysteine, glutathione, dithiothreitol, dihydrolipoic acid, 1,3-dithiopropanol, thioglycolamide, glycerylmonothioglycolate, thioglycolhydrazide, keratinase, hydrazine sulphate, hydrazine disulphate, triisocyanate, guanidine thiglycolate, calcium thioglycolate and cysteamine.

3. A composition according to claim 2 wherein the depilatory agent is potassium thioglycolate.

4. A composition according to claim 1 wherein the RHLB of the total oil phase and the HLB of the surfactant are substantially equal.

5. A composition according to claim 1 wherein the non-polar oil is selected from the group consisting of thick mineral oil, sweet almond oil, isohexane, sunflower seed oil, apricot kernel oil, shea butter, and mixtures thereof.

6. A composition according to claim 1 wherein the surfactant is selected from the group consisting of cetearyl phosphate, cetearyl alcohol, cetearyl glucoside, cetostearyl alcohol, Ceteareth 20, and mixtures thereof.

7. A composition according to claim 1 wherein the polar substance is selected from the group consisting of polypropylene oxide-15 stearyl ether, olive oil, macadamia nut oil, avocado oil, calendula oil, wheat germ oil, cyclomethicone, and mixtures thereof.

8. A composition according to claim 1 which additionally comprises an accelerator that will accelerate the action of the depilatory agent in degrading keratin.

9. A composition according to claim 8 wherein the accelerator is selected from the group consisting of urea, thiourea, dimethyl isosorbide, ethoxydiglycol, methylpropyldiol, and mixtures thereof.

10. A composition according to claim 9 in which the accelerator is urea and is present in the aqueous phase.

11. A composition according to claim 1 further comprising a clay in an amount of from 0.1% to 10% w/w.

12. A composition according to claim 1 which is in the form of a cream.

13. A process for preparing a composition as defined in claim 1 which process comprises the steps of: mixing the oil phase ingredients together at a temperature of from 50° to 80° C.; adding the aqueous phase ingredients at a temperature of from 70° C. to 80° C.; and thereafter adding the depilatory agent at a temperature of from 30° to 40° C.

14. A processing for preparing a composition as defined in claim 1 which process comprises the steps of: mixing the non-polar oil and the surfactant together at a temperature of from 50° to 80° C.; adding the aqueous phase at a temperature of from 70° to 80° C.; and thereafter adding the depilatory agent and polar substance at a temperature of from 30° to 40° C.

15. A process according to claim 14, wherein the mixing and addition steps are effected under conditions of agitation sufficient to aid mixing but insufficient to cause turbulence.

16. A method for removing unwanted hair which comprises the steps of: (1) applying to an area of the body from which depilation is desired a depilatory composition in the form of an oil-in-water emulsion which comprises:

from 2% to 6% w/w of a depilatory agent;

from 4.7% to 66% w/w of an oil phase comprising, as a percentage of the depilatory composition, from 0.2% to 20% w/w of a non-polar oil in the form of droplets having a diameter of from 0.01 to 10 $\mu$m and a polarity index of from 20 to 40 mN/m, from 2% to 20% w/w of a surfactant having a HLB value of from 9 to 12, and from 0.5% to 20% of a polar substance having a polarity index of from 2 to 15 mN/m, the oil phase having a RHLB value of from 9 to 12; and from 5.3% to 34% of an aqueous phase comprising L-arginine and lime as pH regulators, wherein the depilatory agent is present in both the oil phase and the aqueous phase and the depilatory composition is substantially free from tertiary amines; (2) allowing said composition to remain on the skin for sufficient time to degrade keratin present in said hair; and (3) removing said composition together with the unwanted hair.

17. A method according to claim 16 in which, in the composition, the depilatory agent is potassium thioglycolate, and urea is additionally present as an accelerator.

* * * * *